United States Patent [19]
Bandman et al.

[11] Patent Number: 6,054,290
[45] Date of Patent: Apr. 25, 2000

[54] HUMAN VESICLE BINDING PROTEIN

[75] Inventors: Olga Bandman; Phillip R. Hawkins, both of Mountain View; Lynn E. Murry, Portola Valley, all of Calif.

[73] Assignee: Incyte Pharamaceuticals, Inc., Palo Alto, Calif.

[21] Appl. No.: 08/857,213

[22] Filed: May 15, 1997

[51] Int. Cl.[7] ............................ C12N 15/11; C12N 15/85; C07H 21/04
[52] U.S. Cl. ................. 435/69.1; 435/70.1; 435/71.1; 435/71.2; 435/252.3; 435/254.11; 435/320.1; 435/325; 536/23.5
[58] Field of Search .................. 536/23.1, 23.5; 435/69.1, 70.1, 71.1, 71.2, 91.1, 325, 252.3, 254.11, 320.1

[56] References Cited

U.S. PATENT DOCUMENTS 5,472,856  12/1995  Harris et al. .

OTHER PUBLICATIONS

Hillier et al Wash U–Merck Est Project (1995) AA166921.
Hillier et al. Wash U–Merck Est Project (1995) N99770.
Skehel et al Alignment ACU 36779.
D'Esposito et al *Nature Genetics* 13 (Jun. 1996) 227–229.
Ravichandran et al *JBC* 271 (23) (Jun. 1996) 13300–13303.
Ravichandran et al (Apr. 1997) vol. 8 pp. 159–161.

Galli, T., et al., "Tetanus Toxin–mediated Cleavage of Cellubrevin Impairs Exocytosis of Transferrin Receptor–Containing Vesicles in CHO Cells," *The Journal of Cell Biology*, 125(5):1015–1024 (1994).

Link, E., et al., "Cleavage of Cellubrevin by Tetanus Toxin Does Not Affect Fusion of Early Endosomes," *The Journal of Biological Chemistry*, 268(25):18423–18426 (1993).

Skehel, P., et al., "A VAMP–Binding Protein from Aplysia Required for Neurotransmitter Release," *Science*, 269:1580–1582 (1995) (GI 1000368 and GI 1000369).

Bark, I., et al., "Regulated vesicular fusion in neurons: Snapping together the details," *Proc. Natl. Acad. Sci. USA*, 91:4621–4624 (1994).

Skehel, P., et al., (GI 1000368 and GI 1000369) GenBank Sequence Database (Accession U36779) National Center for Biotechnology Information, National Library of Medicine, Bethesda, Maryland, 20894.

*Primary Examiner*—Patricia A. Duffy
*Attorney, Agent, or Firm*—Colette C. Muenzen, Esq.; Incyte Pharmaceuticals, Inc.

[57] ABSTRACT

The present invention provides a human vesicle binding protein (MVBP) and polynucleotides which identify and encode MVBP. The invention also provides expression vectors, host cells, agonists, antibodies and antagonists. In addition, the invention provides methods for producing MVBP and for treating or preventing disorders associated with expression of MVBP.

8 Claims, 7 Drawing Sheets

```
              9          18    27         36         45         54
NNA GTC TTT ATT TTT TAG GTA AAT TCC ATT GAA TCA AAT ATA ACA AAA TTA CAG
             63          72    81         90         99        108
TTT TTG TTT GTA ATG ATC TTT GTT CAC CAC ACA ATC ATA GTA GAA TCA AAA
            117         126   135        144        153        162
GTA ATA TGA GAA CAT AAA ATG ATC AAG GAC AAT GTT TAG TAT AAT TTC TTA
            171         180   189        198        207        216
ATA AAG GTA AAT ATC CCC ATA TTT AGA AAA AAT TGC ATT GCT AGT TGC AAA TCT
            225         234   243        252        261        270
TAA ACA CCT CAG TGC TGA AGG ATC CTG TAT TTC CCC CCA AAG ATC CAG CAG CAC
            279         288   297        306        315        324
GGA GGC TTT CAG AAC ACA AAC TCA AAA CAA ATA TAG TAT TTT CGG GGC AGC ATT TTA
            333         342   351        360        369        378
AGT TTC AGA AAA CCC AAA CAA TCT AAA ACA GAA TCA GGA ATG TGA AAG
            387         396   405        414        423        432
TGA TGG TGC TCT AAA AAT CAA TCT GGA AGC AGA TCT GCC AAC ATA AGA ATG TGG
            441         450   459        468        477        486
TTG AAC AGA GTC TAA CCA GGA AAA GGA GAG ATG CGA ACT CGC CCC TCC CCT

```
                                                                                   540
495         504         513         522         531                                GTC
CTC GCC     GTC CCC     CGA CAG     CGC CCC     CTC TGC     GCT                     V
 L   D       P   T       R   P       Q   R       P   L       C   A 594
549         558         567         576         585                                GTC
TCT CCA     ATG GCG     TCC TCA     GGG ATG     GCC TTC     GAG ATC     CAG CTG     V
             M   A       S   G       M   A       F   E       I   Q       L 648
603         612         621         630         639                                ACT
CTC GAT     CCG CCC     ACA GAC     CTC AAA     TTC AAA     GGC ATG     GCG TCC     T
 L   D       P   P       T   D       L   K       F   K       G   M       A   S 702
657         666         675         684         693                                AAG
ACA AAT     CTT AAA     TTG CGA     AAT CCA     ACA TCG     GAT AGA     CCC TTC     K
 T   N       L   K       R   N       P   S       D   R       P   F       T   V 756
711         720         729         738         747                                CCA
ACT ACA     GCA CCT     CGC TAC     TGT CGG     AGG CCC     AAC AGT     GGA ATT     P
 T   T       A   P       R   Y       C   R       P   N       S   G       I   D 810
765         774         783         792         801                                AAT
GGG TCA     ACT GTG     GTT TCA     GTA ATG     CTA CAG     CCC TTT     GAC TAT     N
 G   S       T   V       V   S       V   M       L   Q       P   F       D   Y 864
819         828         837         846         855                                TTC
GAA AAG     AGT AAA     CAC AAG     TTT ATG     GTA CAG     ACT TTT     TGC TCC     F
 E   K       S   K       H   K       F   M       V   Q       T   F       C   S
```

FIGURE 1B

```
        873             882             891             900             909             918
AGA TAT GAA GCT GTG TGG AAA GAG GCA AAA CCT GAT GAA TTA ATG GAT TCC AAA
 R   Y   E   A   V   W   K   E   A   K   P   D   E   L   M   D   S   K 927             936             945             954             963             972
TTG AGA TCC CCA ATG AAA ATG ATA AAT TGT GAT ATG GAA CCT AGC AAA GCT GTT
 L   R   S   P   M   K   M   I   N   C   D   M   E   P   S   K   A   V 981             990             999            1008            1017            1026
CCA AAT GCA TCT AAG CAA GAC GGA CCC ACG CCA CAA CCA CAC AGT GCT TCA
 P   N   A   S   K   Q   D   G   P   T   P   Q   P   H   S   A   S 1035            1044            1053            1062            1071            1080
CTT AAT GAT ACC GAA ACA AGG AAA CTA ATG GAA GAG TGT AAA AGA CTT CAG GGA
 L   N   D   T   E   T   R   K   L   M   E   E   C   K   R   L   Q   G 1089            1098            1107            1116            1125            1134
GAA ATG AAG CTA TCA GAA GAA AAT CGG CAC CTG AGA GAT GAA GGT TTA AGG
 E   M   K   L   S   E   E   N   R   H   L   R   D   E   G   L   R 1143            1152            1161            1170            1179            1188
CTC AGA AAG GTA GCA CAT TCG GAT AAA CCT GGA TCA ACC TCA ACT GCA TCC TTC
 L   R   K   V   A   H   S   D   K   P   G   S   T   S   T   A   S   F 1197            1206            1215            1224            1233            1242
AGA GAT AAT GTC ACC AGT CCT CTT CCT TCA CTT GTT CTT GTA ATT GCA GCC ATT
 R   D   N   V   T   S   P   L   P   S   L   V   L   V   I   A   A   I
```

FIGURE 1C

```
      1251        1260        1269        1278        1287        1296
TTC ATT GGA TTC TTT CTA GGG AAA TTC ATC TTG TAG AGT GAA GCA TGC AGA GTG
 F   I   G   F   F   L   G   K   F   I   L
      1305        1314        1323        1332        1341        1350
CNN NNN NNN NNN NNN NNN NGA CCA GAA AAA GAT TTG TTT ACC TAC CAT
      1359        1368        1377        1386        1395        1404
TTC ATT GGT AGT ATG GCC CAC GGT GAC CAT TTT TTT GTG TGT ACA GCG TCA TAT
      1413        1422        1431        1440        1449        1458
AGG CTT TGC CTT TAA TGA TCT CTT ACG GTT AGA AAA CAC AAT AAA AAC AAA CTG
      1467        1476        1485        1494        1503        1512
TTC GGC TAC TGG ACA AGG TTG TAT ATT ACC AGA TCA TCA CTA GCA GAT GTC AGT
      1521        1530        1539        1548        1557        1566
TGC ACA TTG AGT CCT TTA TGA AAT TCA TAA ATA AAG AAT TGT TCT TTC TTT GTG
      1575        1584        1593        1602        1611        1620
GTT TTA ATA AGA GTT CAA GAA TTG TTC AGA GTC TTG TAA ATG TTA TTT TAA TAA
      1629        1638        1647        1656        1665        1674
TCC CTT TAA ATT TTA TCT GTT GCT GTT ACC TCT TGA AAT ATG ATT TAT TTA GAT
      1683        1692        1701        1710        1719
TGC TAA TCC CAC TCA TTC AGG AAA TGC CAA GAG GTA TTC CTT GGG GTC T

                          SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
           (A) LENGTH: 236 amino acids
           (B) TYPE: amino acid
           (C) STRANDEDNESS: single
           (D) TOPOLOGY: linear (vii) IMMEDIATE SOURCE:
           (A) LIBRARY: FIBRNGT01
           (B) CLONE: 148415

(xi) SEQUENCE DESCRIPTION: SEQ ID NO:1:

Met Ala Lys Phe Glu Gln Ile Leu Val Leu Asp Pro Pro Thr Asp Leu
1               5                  10                  15

Lys Phe Lys Gly Pro Phe Thr Asp Val Val Thr Thr Asn Leu Lys Leu
                20                  25                  30

Arg Asn Pro Ser Asp Arg Lys Val Cys Phe Lys Val Lys Thr Thr Ala
                35                  40                  45

Pro Arg Arg Tyr Cys Val Arg Pro Asn Ser Gly Ile Ile Asp Pro Gly
 50                  55                  60

Ser Thr Val Thr Val Ser Val Met Leu Gln Pro Phe Asp Tyr Asp Pro
65                  70                  75                  80

Asn Glu Lys Ser Lys His Lys Phe Met Val Gln Thr Phe Cys Ser Thr
                85                  90                  95

Lys His Phe Arg Tyr Glu Ala Val Trp Lys Glu Ala Lys Pro Asp Glu
                100                 105                 110

Leu Met Asp Ser Lys Leu Arg Ser Pro Met Lys Met Ile Asn Cys Asp
                115                 120                 125

Met Glu Pro Ser Lys Ala Val Pro Leu Asn Ala Ser Lys Gln Asp Gly
                130                 135                 140

Pro Thr Pro Gln Pro His Ser Ala Ser Leu Asn Asp Thr Glu Thr Arg
145                 150                 155                 160

Lys Leu Met Glu Glu Cys Lys Arg Leu Gln Gly Glu Met Met Lys Leu
                165                 170                 175

Ser Glu Glu Asn Arg His Leu Arg Asp Glu Gly Leu Arg Leu Arg Lys
                180                 185                 190

Val Ala His Ser Asp Lys Pro Gly Ser Thr Ser Thr Ala Ser Phe Arg
                195                 200                 205

Asp Asn Val Thr Ser Pro Leu Pro Ser Leu Leu Val Val Ile Ala Ala
                210                 215                 220

Ile Phe Ile Gly Phe Phe Leu Gly Lys Phe Ile Leu
225                 230                 235

(2) INFORMATION FOR SEQ ID NO:2:

(i) SEQUENCE CHARACTERISTICS:
           (A) LENGTH: 1721 base pairs
           (B) TYPE: nucleic acid
           (C) STRANDEDNESS: single
```

(D) TOPOLOGY: linear (vii) IMMEDIATE SOURCE:
          (A) LIBRARY: FIBRNGT01
          (B) CLONE: 148415

(xi) SEQUENCE DESCRIPTION: SEQ ID NO:2:

```
AGTCTTTATT TTTTAGGTAA ATTCCATTGA ATCAAATATA ACAAAATTAC AGTTTTTGTT     60

TGTAATGATC TTTGTTCACC ACCACACAAT CATAGTAGAA TCAAAAGTAA TATGAGAACA    120

TAAAATGATC AAGGACATCA ATGTTTAGTA TAATTTCTTA ATAAAGGTAA ATATCCCCAT    180

ATTTAGAAAA AATTGCATTG CTAGTTGCAA ATCTTAAACA CCTCAGTGCT GAAGGATCCT    240

GTATTTCCCC CCAAAGATCC AGCAGCACGG AGGCTTTCAG AACACAAACT CAAAAATATA    300

GTATTTTCGG GGCAGCATTT TAAGTTTCAG AAAACCCAAA CAAAACAAAA CAAAATCAGA    360

ATCAGGAATG TGAAAGTGAT GGTGCTCTAA AAATCAATCT GGAAGCAGAT CTGCCAACAT    420

AAGAATGTGG TTGAACAGAG TCTAACCAGG AAAAGGAGAG ATGCGAACTC GCTCCCCCTC    480

CCCTCTCGCC ATCGTCCCCC GCCCCCAGCG AGCAAGCCGC CCCCTGCTCT GCGCTGTCTC    540

TCCAATGGCG TCCGCCTCAG GGGCCATGGC GAAGTTCGAG CAGATCCTGG TCCTCGATCC    600

GCCCACAGAC CTCAAATTCA AAGGCCCCTT CACAGATGTA GTCACTACAA ATCTTAAATT    660

GCGAAATCCA TCGGATAGAA AAGTGTGTTT CAAAGTGAAG ACTACAGCAC CTCGCCGGTA    720

CTGTGTGAGG CCCAACAGTG GAATTATTGA CCCAGGGTCA ACTGTGACTG TTTCAGTAAT    780

GCTACAGCCC TTTGACTATG ATCCGAATGA AAAGAGTAAA CACAAGTTTA TGGTACAGAC    840

TTTTTGCTCC ACCAAACACT TCAGATATGA AGCTGTGTGG AAAGAGGCAA AACCTGATGA    900

ATTAATGGAT TCCAAATTGA GATCCCCAAT GAAAATGATA AATTGTGATA TGGAACCTAG    960

CAAAGCTGTT CCACTGAATG CATCTAAGCA AGACGGACCC ACGCCACAAC CACACAGTGC   1020

TTCACTTAAT GATACCGAAA CAAGGAAACT AATGGAAGAG TGTAAAAGAC TTCAGGGAGA   1080

AATGATGAAG CTATCAGAAG AAAATCGGCA CCTGAGAGAT GAAGGTTTAA GGCTCAGAAA   1140

GGTAGCACAT TCGGATAAAC CTGGATCAAC CTCAACTGCA TCCTTCAGAG ATAATGTCAC   1200

CAGTCCTCTT CCTTCACTTC TTGTTGTAAT TGCAGCCATT TTCATTGGAT TCTTTCTAGG   1260

GAAATTCATC TTGTAGAGTG AAGCATGCAG AGTGCNNNNN NNNNNNNNNN NNNNNNNNNG   1320

ACCAGAAAAA GATTTGTTTA CCTACCATTT CATTGGTAGT ATGGCCCACG GTGACCATTT   1380

TTTTGTGTGT ACAGCGTCAT ATAGGCTTTG CCTTTAATGA TCTCTTACGG TTAGAAAACA   1440

CAATAAAAAC AAACTGTTCG GCTACTGGAC AAGGTTGTAT ATTACCAGAT CATCACTAGC   1500

AGATGTCAGT TGCACATTGA GTCCTTTATG AAATTCATAA ATAAAGAATT GTTCTTTCTT   1560

TGTGGTTTTA ATAAGAGTTC AAGAATTGTT CAGAGTCTTG TAAATGTTAT TTTAATAATC   1620

CCTTTAAATT TTATCTGTTG CTGTTACCTC TTGAAATATG ATTTATTTAG ATTGCTAATC   1680

CCACTCATTC AGGAAATGCC AAGAGGTATT CCTTGGGGTC T                       1721
```

(2) INFORMATION FOR SEQ ID NO:3:

(i) SEQUENCE CHARACTERISTICS:
        (A) LENGTH: 260 amino acids
        (B) TYPE: amino acid
        (C) STRANDEDNESS: single
        (D) TOPOLOGY: linear (vii) IMMEDIATE SOURCE:
          (A) LIBRARY: GenBank
          (B) CLONE: 1000369

(xi) SEQUENCE DESCRIPTION: SEQ ID NO:3:

-continued

```
Met Ala Ser His Glu Gln Ala Leu Ile Leu Glu Pro Ala Gly Glu Leu
 1               5                  10                  15

Arg Phe Lys Gly Pro Phe Thr Asp Val Val Thr Ala Asp Leu Lys Leu
            20                  25                  30

Ser Asn Pro Thr Asp Arg Arg Ile Cys Phe Lys Val Lys Thr Thr Ala
            35                  40                  45

Pro Lys Arg Tyr Cys Val Arg Pro Asn Ser Gly Ile Leu Glu Pro Lys
     50                  55                  60

Thr Ser Ile Ala Val Ala Val Met Leu Gln Pro Phe Asn Tyr Asp Pro
 65              70                  75                      80

Asn Glu Lys Asn Lys His Lys Phe Met Val Gln Ser Met Tyr Ala Pro
                85                  90                  95

Asp His Val Val Glu Ser Gln Glu Leu Leu Trp Lys Asp Ala Pro Pro
            100                 105                 110

Glu Ser Leu Met Asp Thr Lys Leu Arg Cys Val Phe Glu Met Pro Asp
            115                 120                 125

Gly Ser His Gln Ala Pro Ala Ser Asp Ala Ser Arg Ala Thr Asp Ala
            130                 135                 140

Gly Ala His Phe Ser Glu Ser Ala Leu Glu Asp Pro Thr Val Ala Ser
145                 150                 155                 160

Arg Lys Thr Glu Thr Gln Ser Pro Lys Arg Val Gly Ala Val Gly Ser
                165                 170                 175

Ala Gly Glu Asp Val Lys Lys Leu Gln His Glu Leu Lys Lys Ala Gln
            180                 185                 190

Ser Glu Ile Thr Ser Leu Lys Gly Glu Asn Ser Gln Leu Lys Asp Glu
            195                 200                 205

Gly Ile Arg Leu Arg Lys Val Ala Met Thr Asp Thr Val Ser Pro Thr
    210                 215                 220

Pro Leu Asn Pro Ser Pro Ala Pro Ala Ala Ala Val Arg Ala Phe Pro
225                 230                 235                 240

Pro Val Val Tyr Val Val Ala Ala Ile Ile Leu Gly Leu Ile Ile Gly
                245                 250                 255

Lys Phe Leu Leu
            260
```

```

HUMAN VESICLE BINDING PROTEIN

FIELD OF THE INVENTION

This invention relates to nucleic acid and amino acid sequences of a human vesicle binding protein and to the use of these sequences in the diagnosis, prevention, and treatment of inflammation and disorders of cell proliferation.

BACKGROUND OF THE INVENTION

Synaptobrevins are synaptic vesicle-associated membrane proteins (VAMPs) which were first discovered in rat brain. These proteins were initially thought to be limited to neuronal cells and to function in the movement of vesicles from the plasmalemma of one cell, across the synapse, to the plasmalemma of another cell. Synaptobrevins are now known to occur and function in constitutive vesicle trafficking pathways involving receptor-mediated endocytotic and exocytotic pathways of many non-neuronal cell types. This regulated vesicle trafficking pathway may be blocked by the highly specific action of clostridial neurotoxins which cleave the synaptobrevin molecule.

In vitro studies of various cellular membranes (Galli et al (1994) J Cell Biol 125:1015–24; Link et al (1993) J Biol Chem 268:18423–6) have shown that VAMPS including the synaptobrevins, cellubrevins, and synaptogyrins are widely distributed. These important membrane trafficking proteins appear to participate in axon extension via exocytosis during development, in the release of neurotransmitters and modulatory peptides, and in endocytosis. Endocytotic vesicular transport includes such intracellular events as the fusions and fissions of the nuclear membrane, endoplasmic reticulum, Golgi apparatus, and various inclusion bodies such as peroxisomes or lysosomes. Endocytotic processes appear to be universal in eukaryotic cells as diverse as yeast, *Caenorhabditis elegans*, Drosophila, and mammals.

A synaptobrevin-binding protein required for neurotransmitter release was recently isolated from the neurons of *Aplysia californica*. Expression of the encoding cDNA in bacteria produced a 206 amino acid polypeptide with a molecular mass of 33 kD (VAP-33). The primary structure of VAP-33 showed similarity to an extracellular sperm protein, and functional analysis suggested its association in the exocytosis of synaptic vesicles (Skelhel, P. A. et al. (1995) Science 269: 1580–82).

Elucidation of the interactions between synaptobrevins, docking proteins, and core fusion proteins (Bark I C and Wilson M C (1994) Proc Natl Acad Sci 91:4621–4624) provide means for the regulation of membrane fusion and fission in normal as well as acute and chronic disease situations. The discovery of human vesicle binding protein and the polynucleotides encoding it satisfies a need in the art by providing a means for diagnosis, prevention, and treatment of inflammation and disorders of cell proliferation.

SUMMARY OF THE INVENTION

The present invention features a human vesicle binding protein hereinafter designated MVBP and characterized as having similarity to Aplysia VAMP/synaptobrevin binding protein.

Accordingly, the invention features a substantially purified MVBP having the amino acid sequence shown in SEQ ID NO:1.

One aspect of the invention features isolated and substantially purified polynucleotides that encode MVBP. In a particular aspect, the polynucleotide is the nucleotide sequence of SEQ ID NO:2.

The invention also relates to a polynucleotide sequence comprising the complement of SEQ ID NO:2 or variants thereof. In addition, the invention features polynucleotide sequences which hybridize under stringent conditions to SEQ ID NO:2.

The invention additionally features fragments of the polynucleotide sequences, expression vectors and host cells comprising polynucleotides that encode MVBP. The present invention also features antibodies which bind specifically to MVBP, and pharmaceutical compositions comprising substantially purified MVBP. The invention also features methods for treating inflammation or disorders of cell proliferation using an antagonist of MVBP.

BRIEF DESCRIPTION OF THE FIGURES

FIGS. 1A–D show the amino acid sequence (SEQ ID NO:1) and nucleic acid sequence (SEQ ID NO:2) of human vesicle binding protein (MVBP). The alignment was produced using MacDNAsis PRO™ software (Hitachi Software Engineering Co., Ltd., San Bruno, Calif.).

FIG. 2 shows the amino acid sequence alignments among MVBP (SEQ ID NO:1), and Aplysia VAMP/synaptobrevin binding protein (GI 1000369; SEQ ID NO:3). The alignment was produced using the multisequence alignment program of DNASTAR™ software (DNASTAR Inc, Madison Wis.).

DESCRIPTION OF THE INVENTION

Figure 3A:
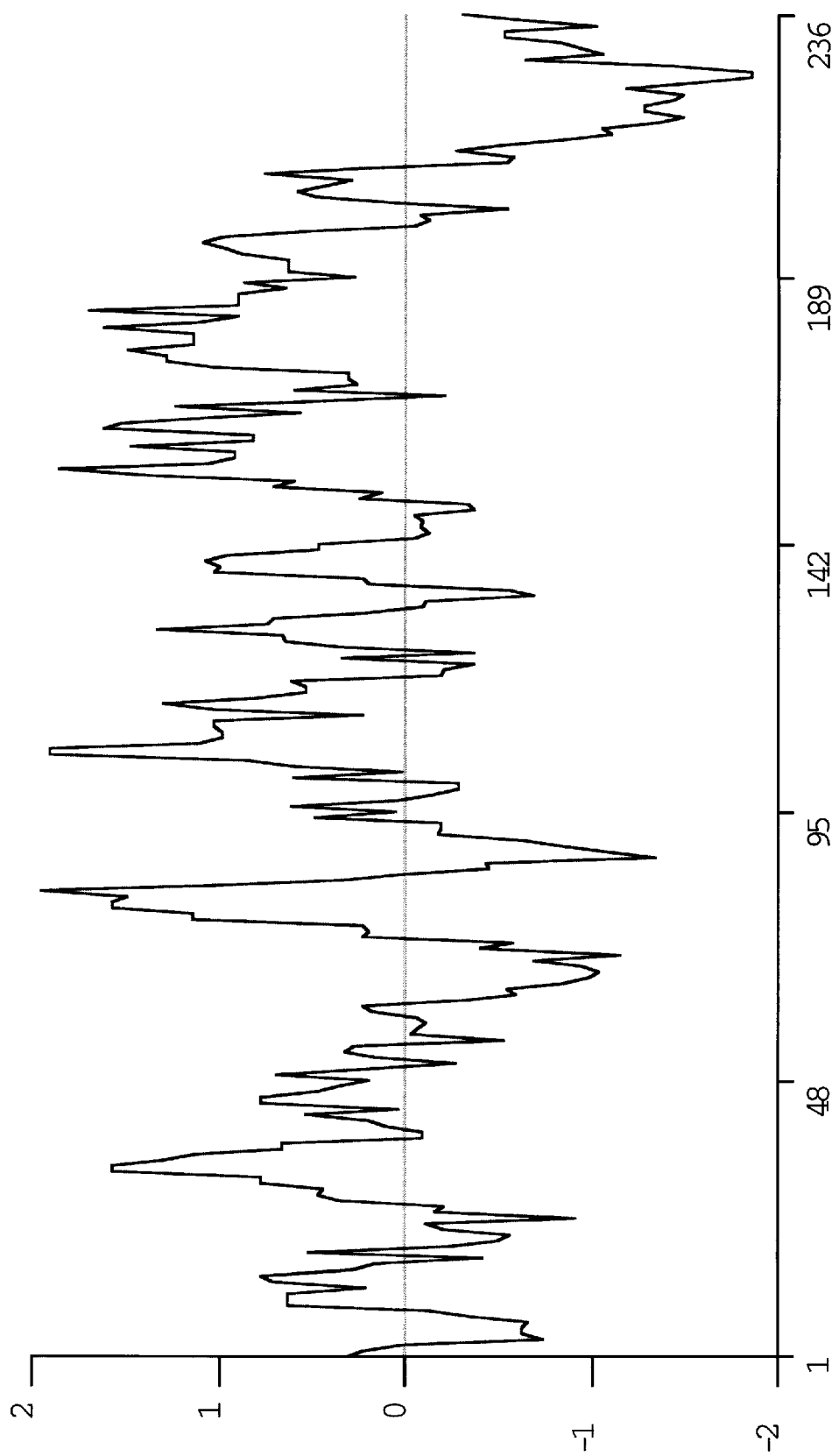
FIGS. 3A and 3B show the hydrophobicity plots (MacDNAsis PRO software) for MVBP (SEQ ID NO: 1) and Aplysia VAMP/synaptobrevin binding protein (SEQ ID NO:3). The positive X axis reflects amino acid position, and the negative Y axis, hydrophobicity.

Before the present proteins, nucleotide sequences, and methods are described, it is understood that this invention is not limited to the particular methodology, protocols, cell lines, vectors, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a host cell" includes a plurality of such host cells, reference to the "antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies which are reported in the publications which might be used in connection with the invention. Nothing herein is to be construed as an admission that the invention is not entitled to antedate such disclosure by virtue of prior invention.

Definitions

"Nucleic acid sequence" as used herein refers to an oligonucleotide, nucleotide, or polynucleotide, and fragments or portions thereof, and to DNA or RNA of genomic or synthetic origin which may be single- or double-stranded, and represent the sense or antisense strand. Similarly, "amino acid sequence" as used herein refers to an oligopeptide, peptide, polypeptide, or protein sequence, and fragments or portions thereof, and to naturally occurring or synthetic molecules.

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule.

"Peptide nucleic acid", as used herein, refers to a molecule which comprises an oligomer to which an amino acid residue, such as lysine, and an amino group have been added. These small molecules, also designated anti-gene agents, stop transcript elongation by binding to their complementary strand of nucleic acid (Nielsen, P. E. et al. (1993) Anticancer Drug Des. 8:53–63).

MVBP, as used herein, refers to the amino acid sequences of substantially purified MVBP obtained from any species, particularly mammalian, including bovine, ovine, porcine, murine, equine, and preferably human, from any source whether natural, synthetic, semi-synthetic, or recombinant.

"Consensus", as used herein, refers to a nucleic acid sequence which has been resequenced to resolve uncalled bases, or which has been extended using XL-PCR™ (Perkin Elmer, Norwalk, Conn.) in the 5' and/or the 3' direction and resequenced, or which has been assembled from the overlapping sequences of more than one Incyte clone using the GELVIEW™ Fragment Assembly system (GCG, Madison, Wis.), or which has been both extended and assembled.

A "variant" of MVBP, as used herein, refers to an amino acid sequence that is altered by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Similar minor variations may also include amino acid deletions or insertions, or both. Guidance in determining which amino acid residues may be substituted, inserted, or deleted without abolishing biological or immunological activity may be found using computer programs well known in the art, for example, DNASTAR software.

A "deletion", as used herein, refers to a change in either amino acid or nucleotide sequence in which one or more amino acid or nucleotide residues, respectively, are absent.

An "insertion" or "addition", as used herein, refers to a change in an amino acid or nucleotide sequence resulting in the addition of one or more amino acid or nucleotide residues, respectively, as compared to the naturally occurring molecule.

A "substitution", as used herein, refers to the replacement of one or more amino acids or nucleotides by different amino acids or nucleotides, respectively.

The term "biologically active", as used herein, refers to a protein having structural, regulatory, or biochemical functions of a naturally occurring molecule. Likewise, "immunologically active" refers to the capability of the natural, recombinant, or synthetic MVBP, or any oligopeptide thereof, to induce a specific immune response in appropriate animals or cells and to bind with specific antibodies.

The term "agonist", as used herein, refers to a molecule which, when bound to MVBP, causes a change in MVBP which modulates the activity of MVBP. Agonists may include proteins, nucleic acids, carbohydrates, or any other molecules which bind to MVBP.

The terms "antagonist" or "inhibitor", as used herein, refer to a molecule which, when bound to MVBP, blocks or modulates the biological or immunological activity of MVBP. Antagonists and inhibitors may include proteins, nucleic acids, carbohydrates, or any other molecules which bind to MVBP.

The term "modulate", as used herein, refers to a change or an alteration in the biological activity of MVBP. Modulation may be an increase or a decrease in protein activity, a change in binding characteristics, or any other change in the biological, functional or immunological properties of MVBP.

The term "mimetic", as used herein, refers to a molecule, the structure of which is developed from knowledge of the structure of MVBP or portions thereof and, as such, is able to effect some or all of the actions of the molecules related to MVBP.

The term "derivative", as used herein, refers to the chemical modification of a nucleic acid encoding MVBP or the encoded MVBP. Illustrative of such modifications would be replacement of hydrogen by an alkyl, acyl, or amino group. A nucleic acid derivative would encode a polypeptide which retains essential biological characteristics of the natural molecule.

The term "substantially purified", as used herein, refers to nucleic or amino acid sequences that are removed from their natural environment, isolated or separated, and are at least 60% free, preferably 75% free, and most preferably 90% free from other components with which they are naturally associated.

"Amplification" as used herein refers to the production of additional copies of a nucleic acid sequence and is generally carried out using polymerase chain reaction (PCR) technologies well known in the art (Dieffenbach, C. W. and G. S. Dveksler (1995) *PCR Primer, a Laboratory Manual*, Cold Spring Harbor Press, Plainview, N.Y.).

The term "hybridization", as used herein, refers to any process by which a strand of nucleic acid binds with a complementary strand through base pairing.

The term "hybridization complex", as used herein, refers to a complex formed between two nucleic acid sequences by virtue of the formation of hydrogen binds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0t$ or $R_0t$ analysis) or between one nucleic acid sequence present in solution and another nucleic acid sequence immobilized on a solid support (e.g., membranes, filters, chips, pins or glass slides to which cells have been fixed for in situ hybridization).

The terms "complementary" or "complementarity", as used herein, refer to the natural binding of polynucleotides under permissive salt and temperature conditions by base-pairing. For example, for the sequence "A-G-T" binds to the complementary sequence "T-C-A". Complementarity between two single-stranded molecules may be "partial", in which only some of the nucleic acids bind, or it may be complete when total complementarity exists between the single stranded molecules. The degree of complementarity between nucleic acid strands has significant effects on the efficiency and strength of hybridization between nucleic acid strands. This is of particular importance in amplification reactions, which depend upon binding between nucleic acids strands.

The term "homology", as used herein, refers to a degree of complementarity. There may be partial homology or complete homology (i.e., identity). A partially complementary sequence is one that at least partially inhibits an identical sequence from hybridizing to a target nucleic acid; it is referred to using the functional term "substantially homologous." The inhibition of hybridization of the completely complementary sequence to the target sequence may be examined using a hybridization assay (Southern or northern blot, solution hybridization and the like) under conditions of low stringency. A substantially homologous sequence or probe will compete for and inhibit the binding (i.e., the hybridization) of a completely homologous sequence or probe to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity); in the absence of non-specific binding, the probe will not hybridize to the second non-complementary target sequence.

As known in the art, numerous equivalent conditions may be employed to comprise either low or high stringency conditions. Factors such as the length and nature (DNA, RNA, base composition) of the sequence, nature of the target (DNA, RNA, base composition, presence in solution or immobilization, etc.), and the concentration of the salts and other components (e.g., the presence or absence of formamide, dextran sulfate and/or polyethylene glycol) are considered and the hybridization solution may be varied to generate conditions of either low or high stringency different from, but equivalent to, the above listed conditions.

The term "stringent conditions", as used herein, is the "stringency" which occurs within a range from about Tm-5° C. (5° C. below the melting temperature (Tm) of the probe) to about 20° C. to 25° C. below Tm. As will be understood by those of skill in the art, the stringency of hybridization may be altered in order to identify or detect identical or related polynucleotide sequences.

The term "antisense", as used herein, refers to nucleotide sequences which are complementary to a specific DNA or RNA sequence. The term "antisense strand" is used in reference to a nucleic acid strand that is complementary to the "sense" strand. Antisense molecules may be produced by any method, including synthesis by ligating the gene(s) of interest in a reverse orientation to a viral promoter which permits the synthesis of a complementary strand. Once introduced into a cell, this transcribed strand combines with natural sequences produced by the cell to form duplexes. These duplexes then block either the further transcription or translation. In this manner, mutant phenotypes may be generated. The designation "negative" is sometimes used in reference to the antisense strand, and "positive" is sometimes used in reference to the sense strand.

The term "portion", as used herein, with regard to a protein (as in "a portion of a given protein") refers to fragments of that protein. The fragments may range in size from four amino acid residues to the entire amino acid sequence minus one amino acid. Thus, a protein "comprising at least a portion of the amino acid sequence of SEQ ID NO:1" encompasses the full-length human MVBP and fragments thereof.

"Transformation", as defined herein, describes a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the host cell being transformed and may include, but is not limited to, viral infection, electroporation, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

The term "antigenic determinant", as used herein, refers to that portion of a molecule that makes contact with a particular antibody (i.e., an epitope). When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

The terms "specific binding" or "specifically binding", as used herein, in reference to the interaction of an antibody and a protein or peptide, mean that the interaction is dependent upon the presence of a particular structure (i.e., the antigenic determinant or epitope) on the protein; in other words, the antibody is recognizing and binding to a specific protein structure rather than to proteins in general. For example, if an antibody is specific for epitope "A", the presence of a protein containing epitope A (or free, unlabeled A) in a reaction containing labeled "A" and the antibody will reduce the amount of labeled A bound to the antibody.

The term "sample", as used herein, is used in its broadest sense. A biological sample suspected of containing nucleic acid encoding MVBP or fragments thereof may comprise a cell, chromosomes isolated from a cell (e.g., a spread of metaphase chromosomes), genomic DNA (in solution or bound to a solid support such as for Southern analysis), RNA (in solution or bound to a solid support such as for northern analysis), cDNA (in solution or bound to a solid support), an extract from cells or a tissue, and the like.

The term "correlates with expression of a polynucleotide", as used herein, indicates that the detection of the presence of ribonucleic acid that is similar to SEQ ID NO:2 by northern analysis is indicative of the presence of mRNA encoding MVBP in a sample and thereby correlates with expression of the transcript from the polynucleotide encoding the protein.

"Alterations" in the polynucleotide of SEQ ID NO: 2, as used herein, comprise any alteration in the sequence of polynucleotides encoding MVBP including deletions, insertions, and point mutations that may be detected using hybridization assays. Included within this definition is the detection of alterations to the genomic DNA sequence which encodes MVBP (e.g., by alterations in the pattern of restriction fragment length polymorphisms capable of hybridizing to SEQ ID NO:2), the inability of a selected fragment of SEQ ID NO:2 to hybridize to a sample of genomic DNA (e.g., using allele-specific oligonucleotide probes), and improper or unexpected hybridization, such as hybridization to a locus other than the normal chromosomal locus for the polynucleotide sequence encoding MVBP (e.g., using fluorescent in situ hybridization [FISH] to metaphase chromosomes spreads).

As used herein, the term "antibody" refers to intact molecules as well as fragments thereof, such as Fa, F(ab')$_2$, and Fv, which are capable of binding the epitopic determinant. Antibodies that bind MVBP polypeptides can be prepared using intact polypeptides or fragments containing small peptides of interest as the immunizing antigen. The polypeptide or peptide used to immunize an animal can be derived from the transition of RNA or synthesized chemically, and can be conjugated to a carrier protein, if desired. Commonly used carriers that are chemically coupled to peptides include bovine serum albumin and thyroglobulin. The coupled peptide is then used to immunize the animal (e.g., a mouse, a rat, or a rabbit).

The term "humanized antibody", as used herein, refers to antibody molecules in which amino acids have been replaced in the non-antigen binding regions in order to more closely resemble a human antibody, while still retaining the original binding ability.

The Invention

The invention is based on the discovery of a human vesicle binding protein (MVBP), the polynucleotides encoding MVBP, and the use of these compositions for the diagnosis, prevention, or treatment of inflammation and disorders of cell proliferation.

Nucleic acids encoding the human MVBP of the present invention were first identified in Incyte Clone 148415 from a fibroblast library (FIBRNGT01) through a computer search for amino acid sequence alignments. A consensus sequence, SEQ ID NO:2, was derived from the following nucleic acid sequences: Incyte Clones 004484 and 009484 (HMCINOT01), 017103 (HUVELPB01), 148415 (FIBRNGT01), 490939 (HNT2AGT01), 607818 (COLNNOT01), 645401 (BRSTTUT02), 814788 (OVARTUT01), and 881095 (THYRNOT02); six of which were initially identified in their respective libraries as unique sequences.

Figure 3B:
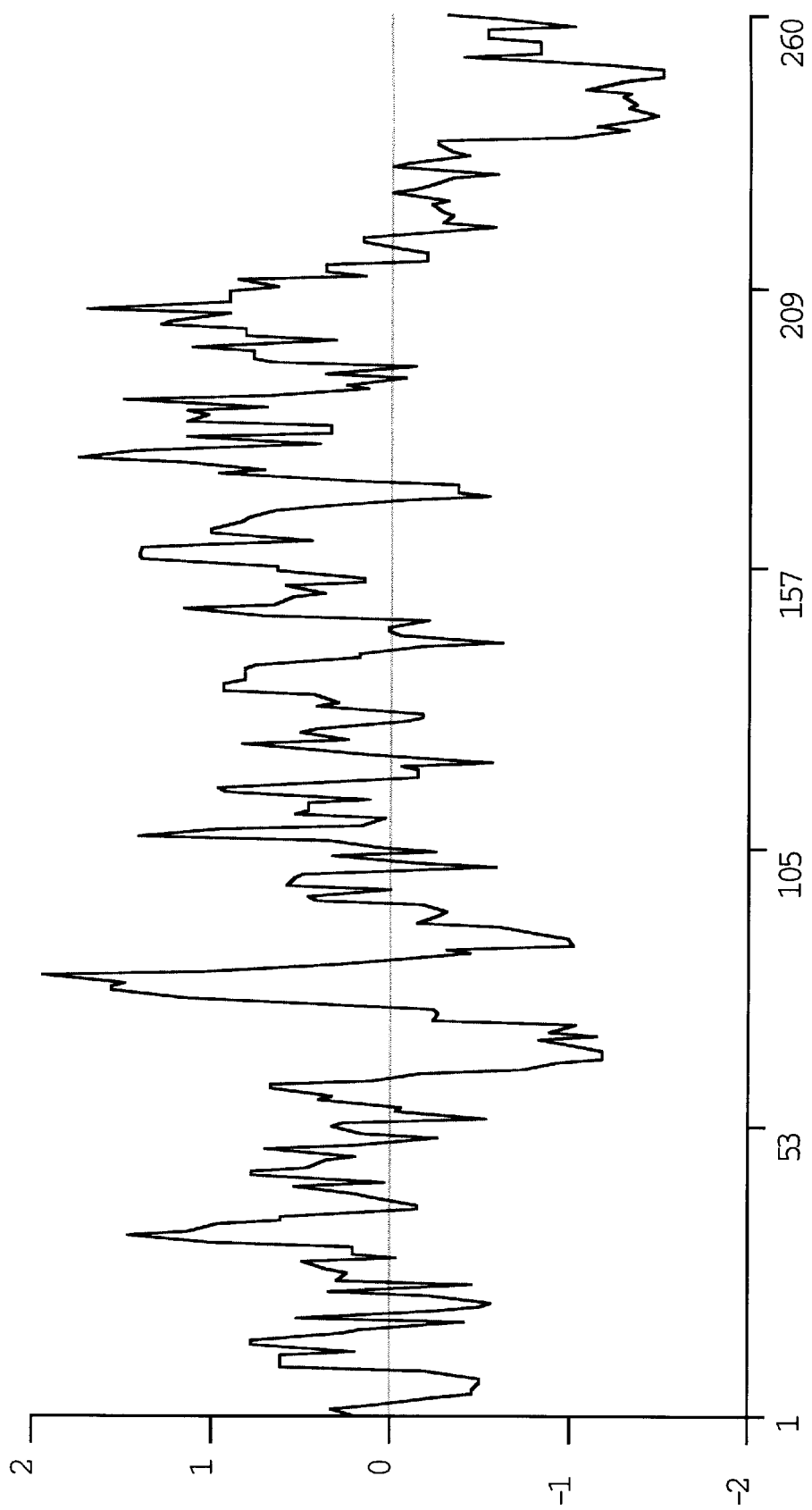

In one embodiment, the invention encompasses a polypeptide comprising the amino acid sequence of SEQ ID NO:1, as shown in FIGS. 1A–D. As shown in FIG. 2, MVBP is 236 amino acids in length; has potential N-linked glycosylation sites at N138, N155, and N210; potential phosphorylation sites at S36, S95, S140, S153, T159, S196, and S206; and potential myristoylation sites at G64 and G200. Of particular note is the presence of a leucine zipper motif, L162–L183, in MVBP. This motif suggests that MVBP binds not only to synaptic vesicle proteins but also to DNA. In particular, MVBP shares approximately 44% identity with Aplysia VAMP/synaptobrevin binding protein (GI 1000369; SEQ ID NO:3). As illustrated by FIGS. 3A and 3B, MVBP with a calculated pI of 9.63 and Aplysia VAMP/synaptobrevin binding protein with a calculated pI of 8.40 have rather similar hydrophobicity plots. Northern analysis showed the expression of MVBP in various cDNA libraries, at least 60% of which were cancerous and at least 17% of which were induced or associated with inflammation. The associations among MVBP, VAMPs and DNA strongly suggest that MVBP is involved in the fusion and fission processes of nuclear membrane during cell division.

The invention also encompasses MVBP variants which retain the biological or other functional activity of MVBP. A preferred MVBP variant is one having at least 85%, and more preferably 90%, amino acid sequence identity to the MVBP amino acid sequence (SEQ ID NO:1). A most preferred MVBP variant is one having at least 95% amino acid sequence identity to SEQ ID NO:1.

The invention also encompasses polynucleotides which encode MVBP. Accordingly, any nucleic acid sequence which encodes the amino acid sequence of MVBP can be used to generate recombinant molecules which express MVBP. In a particular embodiment, the invention encompasses the polynucleotide comprising the nucleic acid sequence of SEQ ID NO:2.

It will be appreciated by those skilled in the art that as a result of the degeneracy of the genetic code, a multitude of nucleotide sequences encoding MVBP, some bearing minimal homology to the nucleotide sequences of any known and naturally occurring gene, may be produced. Thus, the invention contemplates each and every possible variation of nucleotide sequence that could be made by selecting combinations based on possible codon choices. These combinations are made in accordance with the standard triplet genetic code as applied to the nucleotide sequence of naturally occurring MVBP, and all such variations are to be considered as being specifically disclosed.

Although nucleotide sequences which encode MVBP and its variants are preferably capable of hybridizing to the nucleotide sequence of the naturally occurring MVBP under appropriately selected conditions of stringency, it may be advantageous to produce nucleotide sequences encoding MVBP or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding MVBP and its derivatives without altering the encoded amino acid sequences include the production of RNA transcripts having more desirable properties, such as a greater half-life, than transcripts produced from the naturally occurring sequence.

The invention also encompasses production of DNA sequences, or portions thereof, which encode MVBP and its derivatives, entirely by synthetic chemistry. After production, the synthetic sequence may be inserted into any of the many available expression vectors and cell systems using reagents that are well known in the art at the time of the filing of this application. Moreover, synthetic chemistry may be used to introduce mutations into a sequence encoding MVBP or any portion thereof.

Also encompassed by the invention are polynucleotide sequences that are capable of hybridizing to the claimed nucleotide sequences, and in particular, those shown in SEQ ID NO:2, under various conditions of stringency. Hybridization conditions are based on the melting temperature (Tm) of the nucleic acid binding complex or probe, as taught in Wahl, G. M. and S. L. Berger (1987; Methods Enzymol. 152:399–407) and Kimmel, A. R. (1987; Methods Enzymol. 152:507–511), and may be used at a defined stringency.

Altered nucleic acid sequences encoding MVBP which are encompassed by the invention include deletions, insertions, or substitutions of different nucleotides resulting in a polynucleotide that encodes the same or a functionally equivalent MVBP. The encoded protein may also contain deletions, insertions, or substitutions of amino acid residues which produce a silent change and result in a functionally equivalent MVBP. Deliberate amino acid substitutions may be made on the basis of similarity in polarity, charge, solubility, hydrophobicity, hydrophilicity, and/or the amphipathic nature of the residues as long as the biological activity of MVBP is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine; glycine and alanine; asparagine and glutamine; serine and threonine; phenylalanine and tyrosine.

Also included within the scope of the present invention are alleles of the genes encoding MVBP. As used herein, an "allele" or "allelic sequence" is an alternative form of the gene which may result from at least one mutation in the nucleic acid sequence. Alleles may result in altered mRNAs or polypeptides whose structure or function may or may not be altered. Any given gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

Methods for DNA sequencing which are well known and generally available in the art may be used to practice any embodiments of the invention. The methods may employ such enzymes as the Klenow fragment of DNA polymerase I, Sequenase® (US Biochemical Corp, Cleveland, Ohio), Taq polymerase (Perkin Elmer), thermostable T7 polymerase (Amersham, Chicago, Ill.), or combinations of recombinant polymerases and proofreading exonucleases such as the ELONGASE Amplification System marketed by Gibco BRL (Gaithersburg, Md.). Preferably, the process is automated with machines such as the Hamilton Micro Lab 2200 (Hamilton, Reno, Nev.), Peltier Thermal Cycler (PTC200; MJ Research, Watertown, Mass.) and the ABI 377 DNA sequencers (Perkin Elmer).

The nucleic acid sequences encoding MVBP may be extended utilizing a partial nucleotide sequence and employing various methods known in the art to detect upstream sequences such as promoters and regulatory elements. For example, one method which may be employed, "restriction-site" PCR, uses universal primers to retrieve unknown sequence adjacent to a known locus (Sarkar, G. (1993) PCR Methods Applic. 2:318–322). In particular, genomic DNA is first amplified in the presence of primer to linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region (Triglia, T. et al. (1988) Nucleic Acids Res. 16:8186). The primers may be designed using OLIGO 4.06 Primer Analysis software (National Biosciences Inc., Plymouth, Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Another method which may be used is capture PCR which involves PCR amplification of DNA fragments adjacent to a known sequence in human and yeast artificial chromosome DNA (Lagerstrom, M. et al. (1991) PCR Methods Applic. 1:111–119). In this method, multiple restriction enzyme digestions and ligations may also be used to place an engineered double-stranded sequence into an unknown portion of the DNA molecule before performing PCR.

Another method which may be used to retrieve unknown sequences is that of Parker, J. D. et al. (1991; Nucleic Acids Res. 19:3055–3060). Additionally, one may use PCR, nested primers, and PromoterFinder™ libraries to walk in genomic DNA (Clontech, Palo Alto, Calif.). This process avoids the need to screen libraries and is useful in finding intron/exon junctions.

When screening for full-length cDNAs, it is preferable to use libraries that have been size-selected to include larger cDNAs. Also, random-primed libraries are preferable, in that they will contain more sequences which contain the 5' regions of genes. Use of a randomly primed library may be especially preferable for situations in which an oligo d(T) library does not yield a full-length cDNA. Genomic libraries may be useful for extension of sequence into the 5' and 3' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and detection of the emitted wavelengths by a charge coupled devise camera. Output/light intensity may be converted to electrical signal using appropriate software (e.g. Genotyper™ and Sequence Navigator™, Perkin Elmer) and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode MVBP, or fusion proteins or functional equivalents thereof, may be used in recombinant DNA molecules to direct expression of MVBP in appropriate host cells. Due to the inherent degeneracy of the genetic code, other DNA sequences which encode substantially the same or a functionally equivalent amino acid sequence may be produced and these sequences may be used to clone and express MVBP.

As will be understood by those of skill in the art, it may be advantageous to produce MVBP-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence.

The nucleotide sequences of the present invention can be engineered using methods generally known in the art in order to alter MVBP encoding sequences for a variety of reasons, including but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants, or introduce mutations, and so forth.

In another embodiment of the invention, natural, modified, or recombinant nucleic acid sequences encoding MVBP may be ligated to a heterologous sequence to encode a fusion protein. For example, to screen peptide libraries for inhibitors of MVBP activity, it may be useful to encode a chimeric MVBP protein that can be recognized by a commercially available antibody. A fusion protein may also be engineered to contain a cleavage site located between the MVBP encoding sequence and the heterologous protein sequence, so that MVBP may be cleaved and purified away from the heterologous moiety.

In another embodiment, sequences encoding MVBP may be synthesized, in whole or in part, using chemical methods well known in the art (see Caruthers, M. H. et al. (1980) Nucl. Acids Res. Symp. Ser. 215–223, Horn, T. et al. (1980) Nucl. Acids Res. Symp. Ser. 225–232). Alternatively, the protein itself may be produced using chemical methods to synthesize the amino acid sequence of MVBP, or a portion thereof. For example, peptide synthesis can be performed using various solid-phase techniques (Roberge, J. Y. et al. (1995) Science 269:202–204) and automated synthesis may be achieved, for example, using the ABI 43 1A Peptide Synthesizer (Perkin Elmer).

The newly synthesized peptide may be substantially purified by preparative high performance liquid chromatography (e.g., Creighton, T. (1983) *Proteins, Structures and Molecular Principles*, WH Freeman and Co., New York, N.Y.). The composition of the synthetic peptides may be confirmed by amino acid analysis or sequencing (e.g., the Edman degradation procedure; Creighton, supra). Additionally, the amino acid sequence of MVBP, or any part thereof, may be altered during direct synthesis and/or combined using chemical methods with sequences from other proteins, or any part thereof, to produce a variant polypeptide.

In order to express a biologically active MVBP, the nucleotide sequences encoding MVBP or functional equivalents, may be inserted into appropriate expression vector, i.e., a vector which contains the necessary elements for the transcription and translation of the inserted coding sequence.

Methods which are well known to those skilled in the art may be used to construct expression vectors containing sequences encoding MVBP and appropriate transcriptional and translational control elements. These methods include in vitro recombinant DNA techniques, synthetic techniques, and in vivo genetic recombination. Such techniques are described in Sambrook, J. et al. (1989) *Molecular Cloning, A Laboratory Manual*, Cold Spring Harbor Press, Plainview, N.Y., and Ausubel, F. M. et al. (1989) *Current Protocols in Molecular Biology*, John Wiley & Sons, New York, N.Y.

A variety of expression vector/host systems may be utilized to contain and express sequences encoding MVBP. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems.

The "control elements" or "regulatory sequences" are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the Bluescript® phagemid (Stratagene, LaJolla, Calif.) or pSport1™ plasmid (Gibco/BRL) and the like may be used. The baculovirus polyhedrin promoter may be used in insect cells. Promoters or enhancers derived from the genomes of plant cells (e.g., heat shock, RUBISCO; and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding MVBP, vectors based on SV40 or EBV may be used with an appropriate selectable marker.

In bacterial systems, a number of expression vectors may be selected depending upon the use intended for MVBP. For example, when large quantities of MVBP are needed for the induction of antibodies, vectors which direct high level expression of fusion proteins that are readily purified may be used. Such vectors include, but are not limited to, the multifunctional *E. coli* cloning and expression vectors such as Bluescript® (Stratagene), in which the sequence encoding MVBP may be ligated into the vector in frame with sequences for the amino-terminal Met and the subsequent 7 residues of β-galactosidase so that a hybrid protein is produced; pIN vectors (Van Heeke, G. and S. M. Schuster (1989) J. Biol. Chem. 264:5503–5509); and the like. pGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase, and PGH may be used. For reviews, see Ausubel et al. (supra) and Grant et al. (1987) Methods Enzymol. 153:516–544.

In cases where plant expression vectors are used, the expression of sequences encoding MVBP may be driven by any of a number of promoters. For example, viral promoters such as the 35S and 19S promoters of CaMV may be used alone or in combination with the omega leader sequence from TMV (Takamatsu, N. (1987) EMBO J. 6:307–311). Alternatively, plant promoters such as the small subunit of RUBISCO or heat shock promoters may be used (Coruzzi, G. et al. (1984) EMBO J. 3:1671–1680; Broglie, R. et al. (1984) Science 224:838–843; and Winter, J. et al. (1991) Results Probl. Cell Differ. 17:85–105). These constructs can be introduced into plant cells by direct DNA transformation or pathogen-mediated transfection. Such techniques are described in a number of generally available reviews (see, for example, Hobbs, S. or Murry, L. E. in McGraw Hill *Yearbook of Science and Technology* (1992) McGraw Hill, New York, N.Y.; pp. 191–196.

An insect system may also be used to express MVBP. For example, in one such system, *Autographa californica* nuclear polyhedrosis virus (AcNPV) is used as a vector to express foreign genes in *Spodoptera frugiperda* cells or in Trichoplusia larvae. The sequences encoding MVBP may be cloned into a non-essential region of the virus, such as the polyhedrin gene, and placed under control of the polyhedrin promoter. Successful insertion of MVBP will render the polyhedrin gene inactive and produce recombinant virus lacking coat protein. The recombinant viruses may then be used to infect, for example, *S. frugiperda* cells or Trichoplusia larvae in which MVBP may be expressed (Engelhard, E. K. et al. (1994) Proc. Nat. Acad. Sci. 91:3224–3227).

In mammalian host cells, a number of viral-based expression systems may be utilized. In cases where an adenovirus is used as an expression vector, sequences encoding MVBP may be ligated into an adenovirus transcription/translation complex consisting of the late promoter and tripartite leader sequence. Insertion in a non-essential E1 or E3 region of the viral genome may be used to obtain a viable virus which is capable of expressing MVBP in infected host cells (Logan, J. and Shenk, T. (1984) Proc. Natl. Acad. Sci. 81:3655–3659). In addition, transcription enhancers, such as the Rous sarcoma virus (RSV) enhancer, may be used to increase expression in mammalian host cells.

Specific initiation signals may also be used to achieve more efficient translation of sequences encoding MVBP. Such signals include the ATG initiation codon and adjacent sequences. In cases where sequences encoding MVBP, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) Results Probl. Cell Differ. 20:125–162).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells such as CHO, HeLa, MDCK, HEK293, and WI38, which have specific cellular machinery and characteristic mechanisms for such post-translational activities, may be chosen to ensure the correct modification and processing of the foreign protein.

For long-term, high-yield production of recombinant proteins, stable expression is preferred. For example, cell lines which stably express MVBP may be transformed using expression vectors which may contain viral origins of replication and/or endogenous expression elements and a selectable marker gene on the same or on a separate vector. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) Cell 11:223–32) and adenine phosphoribosyltransferase (Lowy, I. et al. (1980) Cell 22:817–23) genes which can be employed in $tk^-$ or $aprt^-$ cells, respectively. Also, antimetabolite, antibiotic or herbicide resistance can be used as the basis for selection; for example, dhfr which confers resistance to methotrexate (Wigler, M. et al. (1980) Proc. Natl. Acad. Sci. 77:3567–70); npt, which confers resistance to the aminoglycosides neomycin and G-418 (Colbere-Garapin, F. et al (1981) J. Mol. Biol. 150:1–14) and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) Proc. Natl. Acad. Sci. 85:8047–51). Recently, the use of visible markers has gained popularity with such markers as anthocyanins, β glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) Methods Mol. Biol. 55:121–131).

Although the presence/absence of marker gene expression suggests that the gene of interest is also present, its presence and expression may need to be confirmed. For example, if the sequence encoding MVBP is inserted within a marker gene sequence, recombinant cells containing sequences encoding MVBP can be identified by the absence of marker gene function. Alternatively, a marker gene can be placed in tandem with a sequence encoding MVBP under the control of a single promoter. Expression of the marker gene in response to induction or selection usually indicates expression of the tandem gene as well.

Alternatively, host cells which contain the nucleic acid sequence encoding MVBP and express MVBP may be identified by a variety of procedures known to those of skill in the art. These procedures include, but are not limited to, DNA-DNA or DNA-RNA hybridizations and protein bioassay or immunoassay techniques which include membrane, solution, or chip based technologies for the detection and/or quantification of nucleic acid or protein.

The presence of polynucleotide sequences encoding MVBP can be detected by DNA-DNA or DNA-RNA hybridization or amplification using probes or portions or fragments of polynucleotides encoding MVBP. Nucleic acid amplification based assays involve the use of oligonucleotides or oligomers based on the sequences encoding MVBP to detect transformants containing DNA or RNA encoding MVBP. As used herein "oligonucleotides" or "oligomers" refer to a nucleic acid sequence of at least about 10 nucleotides and as many as about 60 nucleotides, preferably about 15 to 30 nucleotides, and more preferably about 20–25 nucleotides, which can be used as a probe or amplimer.

A variety of protocols for detecting and measuring the expression of MVBP, using either polyclonal or monoclonal antibodies specific for the protein are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on MVBP is preferred, but a competitive binding assay may be employed. These and other assays are described, among other places, in Hampton, R. et al. (1990; *Serological Methods, a Laboratory Manual*, APS Press, St Paul, Minn.) and Maddox, D. E. et al. (1983; J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding MVBP include oligolabeling, nick translation, end-labeling or PCR amplification using a labeled nucleotide. Alternatively, the sequences encoding MVBP, or any portions thereof may be cloned into a vector for the production of an mRNA probe.

Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits (Pharmacia & Upjohn, (Kalamazoo, Mich.); Promega (Madison Wis.); and U.S. Biochemical Corp., Cleveland, Ohio). Suitable reporter molecules or labels, which may be used, include radionuclides, enzymes, fluorescent, chemiluminescent, or chromogenic agents as well as substrates, cofactors, inhibitors, magnetic particles, and the like.

Host cells transformed with nucleotide sequences encoding MVBP may be cultured under conditions suitable for the expression and recovery of the protein from cell culture. The protein produced by a recombinant cell may be secreted or contained intracellularly depending on the sequence and/or the vector used. As will be understood by those of skill in the art, expression vectors containing polynucleotides which encode MVBP may be designed to contain signal sequences which direct secretion of MVBP through a prokaryotic or eukaryotic cell membrane. Other recombinant constructions may be used to join sequences encoding MVBP to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (Invitrogen, San Diego, Calif.) between the purification domain and MVBP may be used to facilitate purification. One such expression vector provides for expression of a fusion protein containing MVBP and a nucleic acid encoding 6 histidine residues preceding a thioredoxin or an enterokinase cleavage site. The histidine residues facilitate purification on IMIAC (immobilized metal ion affinity chromatography as described in Porath, J. et al. (1992, Prot. Exp. Purif. 3: 263–281) while the enterokinase cleavage site provides a means for purifying MVBP from the fusion protein. A Such antibodies may include, but are not limited to, polyclonal, monoclonal, chimeric, single chain, Fab fragments, and fragments produced by a Fab expression library. Neutralizing antibodies, (i.e., those which inhibit dimer formation) are especially preferred for therapeutic use.

For the production of antibodies, various hosts including goats, rabbits, rats, mice, humans, and others, may be immunized by injection with MVBP or any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and *Corynebacterium parvum* are especially preferable.

It is preferred that the peptides, fragments, or oligopeptides used to induce antibodies to MVBP have an amino acid sequence consisting of at least five amino acids, and more preferably at least 10 amino acids. It is also preferable that they are identical to a portion of the amino acid sequence of the natural protein, and they may contain the entire amino acid sequence of a small, naturally occurring molecule. Short stretches of MVBP amino acids may be fused with those of another protein such as keyhole limpet hemocyanin and antibody produced against the chimeric molecule.

Monoclonal antibodies to MVBP may be prepared using any technique which provides for the production of antibody molecules by continuous cell lines in culture. These include, but are not limited to, the hybridoma technique, the human B-cell hybridoma technique, and the EBV-hybridoma technique (Kohler, G. et al. (1975) Nature 256:495–497; Kozbor, D. et al. (1985) J. Immunol. Methods 81:31–42; Cote, R. J. et al. (1983) Proc. Natl. Acad. Sci. 80:2026–2030; Cole, S. P. et al. (1984) Mol. Cell Biol. 62:109–120).

In addition, techniques developed for the production of "chimeric antibodies", the splicing of mouse antibody genes to human antibody genes to obtain a molecule with appropriate antigen specificity and biological activity can be used (Morrison, S. L. et al. (1984) Proc. Natl. Acad. Sci. 81:6851–6855; Neuberger, M. S. et al. (1984) Nature 12:604–608; Takeda, S. et al. (1985) Nature 314:452–454). Alternatively, techniques described for the production of single chain antibodies may be adapted, using methods known in the art, to produce MVBP-specific single chain antibodies. Antibodies with related specificity, but of distinct idiotypic composition, may be generated by chain shuffling from random combinatorial immunoglobin libraries (Burton D. R. (1991) Proc. Natl. Acad. Sci. 88:11120–3).

Antibodies specific for MVBP may also be produced by inducing in vivo production in the lymphocyte population or by screening recombinant immunoglobulin libraries or panels of highly specific binding reagents as disclosed in the literature (Orlandi, R. et al. (1989) Proc. Natl. Acad. Sci. 86: 3833–3837; Winter, G. et al. (1991) Nature 349:293–299).

Antibody fragments which contain specific binding sites for MVBP may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse, W. D. et al. (1989) Science 254:1275–1281).

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between MVBP and its specific antibody. A two-site, monoclonal-based immunoassay utilizing monoclonal antibodies reactive to two non-interfering MVBP epitopes is preferred, but a competitive binding assay may also be employed (Maddox, supra).

In another embodiment of the invention, the polynucleotides encoding MVBP, or any fragment thereof, or antisense molecules, may be used for therapeutic purposes. In one aspect, antisense to the polynucleotide encoding MVBP may be used in situations in which it would be desirable to block the transcription of the mRNA. In particular, cells may be transformed with sequences complementary to polynucleotides encoding MVBP. Thus, antisense molecules may be used to modulate MVBP activity, or to achieve regulation of ene function. Such technology is now well known in the art, and sense or antisense oligomers or larger fragments, can be designed from various locations along the coding or control regions of sequences encoding MVBP.

Expression vectors derived from retro viruses, adenovirus, herpes or vaccinia viruses, or from various bacterial plasmids may be used for delivery of nucleotide sequences to the targeted organ, tissue or cell population. Methods which are well known to those skilled in the art can be used to construct recombinant vectors which will express antisense molecules complementary to the polynucleotides of the gene encoding MVBP. These techniques are described both in Sambrook et al. (supra) and in Ausubel et al. (supra).

Genes encoding MVBP can be turned off by transforming a cell or tissue with expression vectors which express high levels of a polynucleotide or fragment thereof which encodes MVBP. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector and even longer if appropriate replication elements are part of the vector system.

As mentioned above, modifications of gene expression can be obtained by designing antisense molecules, DNA, RNA, or PNA, to the control regions of the gene encoding MVBP, i.e., the promoters, enhancers, and introns. Oligonucleotides derived from the transcription initiation site, e.g., between positions −10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature (Gee, J. E. et al. (1994) In: Huber, B. E. and B. I. Carr, *Molecular and Immunologic Approaches*, Futura Publishing Co., Mt. Kisco, N.Y.). The antisense molecules may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. Examples which may be used include engineered hammerhead motif ribozyme molecules that can specifically and efficiently catalyze endonucleolytic cleavage of sequences encoding MVBP.

Specific ribozyme cleavage sites within any potential RNA target are initially identified by scanning the target molecule for ribozyme cleavage sites which include the following sequences: GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Antisense molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding MVBP. Such DNA sequences may be incorporated into a wide variety of vectors with suitable RNA polymerase promoters such as T7 or SP6. Alternatively, these cDNA constructs that synthesize antisense RNA constitutively or inducibly can be introduced into cell lines, cells, or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection and by liposome injections may be achieved using methods which are well known in the art.

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical composition, in conjunction with a pharmaceutically acceptable carrier, for any of the therapeutic effects discussed above. Such pharmaceutical compositions may consist of MVBP, antibodies to MVBP, mimetics, agonists, antagonists, or inhibitors of MVBP. The compositions may be administered alone or in combination with at least one other agent, such as stabilizing compound, which may be administered in any sterile, biocompatible pharmaceutical carrier, including, but not limited to, saline, buffered saline, dextrose, and water. The compositions may be administered to a patient alone, or in combination with other agents, drugs or hormones.

The pharmaceutical compositions utilized in this invention may be administered by any number of routes including, but not limited to, oral, intravenous, intramuscular, intraarterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol;

starch from corn, wheat, rice, potato, or other plants; cellulose, such as methyl cellulose, hydroxypropylmethylcellulose, or sodium carboxymethylcellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks's solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation may be a lyophilized powder which may contain any or all of the following: 1–50 mM histidine, 0.1%–2% sucrose, and 2–7% mannitol, at a pH range of 4.5 to 5.5, that is combined with buffer prior to use.

After pharmaceutical compositions have been prepared, they can be placed in an appropriate container and labeled for treatment of an indicated condition. For administration of MVBP, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells, or in animal models, usually mice, rabbits, dogs, or pigs. The animal model may also be used to determine the appropriate concentration range and route of administration. Such information can then be used to determine useful doses and routes for administration in humans.

A therapeutically effective dose refers to that amount of active ingredient, for example MVBP or fragments thereof, antibodies of MVBP, agonists, antagonists or inhibitors of MVBP, which ameliorates the symptoms or condition. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50. Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active moiety or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

Diagnostics

In another embodiment, antibodies which specifically bind MVBP may be used for the diagnosis of conditions or diseases characterized by expression of MVBP, or in assays to monitor patients being treated with MVBP, agonists, antagonists or inhibitors. The antibodies useful for diagnostic purposes may be prepared in the same manner as those described above for therapeutics. Diagnostic assays for MVBP include methods which utilize the antibody and a label to detect MVBP in human body fluids or extracts of cells or tissues. The antibodies may be used with or without modification, and may be labeled by joining them, either covalently or non-covalently, with a reporter molecule. A wide variety of reporter molecules which are known in the art may be used, several of which are described above.

A variety of protocols including ELISA, RIA, and FACS for measuring MVBP are known in the art and provide a basis for diagnosing altered or abnormal levels of MVBP expression. Normal or standard values for MVBP expression are established by combining body fluids or cell extracts taken from normal mammalian subjects, preferably human, with antibody to MVBP under conditions suitable for complex formation The amount of standard complex formation may be quantified by various methods, but preferably by photometric, means. Quantities of MVBP expressed in subject, control and disease, samples from biopsied tissues are compared with the standard values. Deviation between standard and subject values establishes the parameters for diagnosing disease.

In another embodiment of the invention, the polynucleotides encoding MVBP may be used for diagnostic purposes. The polynucleotides which may be used include oligonucleotide sequences, antisense RNA and DNA molecules, and PNAs. The polynucleotides may be used to detect and quantitate gene expression in biopsied tissues in which expression of MVBP may be correlated with disease. The diagnostic assay may be used to distinguish between absence, presence, and excess expression of MVBP, and to monitor regulation of MVBP levels during therapeutic intervention.

In one aspect, hybridization with PCR probes which are capable of detecting polynucleotide sequences, including genomic sequences, encoding MVBP or closely related molecules, may be used to identify nucleic acid sequences which encode MVBP. The specificity of the probe, whether it is made from a highly specific region, e.g., 10 unique nucleotides in the 5' regulatory region, or a less specific region, e.g., especially in the 3' coding region, and the stringency of the hybridization or amplification (maximal, high, intermediate, or low) will determine whether the probe identifies only naturally occurring sequences encoding MVBP, alleles, or related sequences.

Probes may also be used for the detection of related sequences, and should preferably contain at least 50% of the nucleotides from any of the MVBP encoding sequences. The hybridization probes of the subject invention may be DNA or RNA and derived from the nucleotide sequence of SEQ ID NO:2 or from genomic sequence including promoter, enhancer elements, and introns of the naturally occurring MVBP.

Means for producing specific hybridization probes for DNAs encoding MVBP include the cloning of nucleic acid sequences encoding MVBP or MVBP derivatives into vectors for the production of mRNA probes. Such vectors are known in the art, commercially available, and may be used to synthesize RNA probes in vitro by means of the addition of the appropriate RNA polymerases and the appropriate labeled nucleotides. Hybridization probes may be labeled by a variety of reporter groups, for example, radionuclides such as 32P or 35S, or enzymatic labels, such as alkaline phosphatase coupled to the probe via avidin/biotin coupling systems, and the like.

Polynucleotide sequences encoding MVBP may be used for the diagnosis of disorders associated with the expression of MVBP. Examples of such disorders include: adenocarcinoma, leukemia, lymphoma, melanoma, myeloma, sarcoma, and teratocarcinoma; and particularly cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; and AIDS, Addison's disease, adult respiratory distress syndrome, allergies, anemia, asthma, atherosclerosis, bronchitis, cholecystus, Crohn's disease, ulcerative colitis, atopic dermatitis, dermatomyositis, diabetes mellitus, emphysema, atrophic gastritis, glomerulonephritis, gout, Graves' disease, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjögren's syndrome, and autoimmune thyroiditis; complications of cancer, hemodialysis, extracorporeal circulation; viral, bacterial, fungal, parasitic, protozoal, and helminthic infections and trauma. The polynucleotide sequences encoding MVBP may be used in Southern or northern analysis, dot blot, or other membrane-based technologies; in PCR technologies; or in dip stick, pIN, ELISA or chip assays utilizing fluids or tissues from patient biopsies to detect altered MVBP expression. Such qualitative or quantitative methods are well known in the art.

In a particular aspect, the nucleotide sequences encoding MVBP may be useful in assays that detect activation or induction of various cancers, particularly those mentioned above. The nucleotide sequences encoding MVBP may be labeled by standard methods, and added to a fluid or tissue sample from a patient under conditions suitable for the formation of hybridization complexes. After a suitable incubation period, the sample is washed and the signal is quantitated and compared with a standard value. If the amount of signal in the biopsied or extracted sample is significantly altered from that of a comparable control sample, the nucleotide sequences have hybridized with nucleotide sequences in the sample, and the presence of altered levels of nucleotide sequences encoding MVBP in the sample indicates the presence of the associated disease. Such assays may also be used to evaluate the efficacy of a particular therapeutic treatment regimen in animal studies, in clinical trials, or in monitoring the treatment of an individual patient.

In order to provide a basis for the diagnosis of disease associated with expression of MVBP, a normal or standard profile for expression is established. This may be accomplished by combining body fluids or cell extracts taken from normal subjects, either animal or human, with a sequence, or a fragment thereof, which encodes MVBP, under conditions suitable for hybridization or amplification. Standard hybridization may be quantified by comparing the values obtained from normal subjects with those from an experiment where a known amount of a substantially purified polynucleotide is used. Standard values obtained from normal samples may be compared with values obtained from samples from patients who are symptomatic for disease. Deviation between standard and subject values is used to establish the presence of disease.

Once disease is established and a treatment protocol is initiated, hybridization assays may be repeated on a regular basis to evaluate whether the level of expression in the patient begins to approximate that which is observed in the normal patient. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding MVBP may involve the use of PCR. Such oligomers may be chemically synthesized, generated enzymatically, or produced from a recombinant source. Oligomers will preferably consist of two nucleotide sequences, one with sense orientation (5'→3') and another with antisense (3'←5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Methods which may also be used to quantitate the expression of MVBP include radiolabeling or biotinylating nucleotides, coamplification of a control nucleic acid, and standard curves onto which the experimental results are interpolated (Melby, P. C. et al. (1993) J. Immunol. Methods, 159:235–244; Duplaa, C. et al. (1993) Anal. Biochem. 229–236). The speed of quantitation of multiple samples may be accelerated by running the assay in an ELISA format where the oligomer of interest is presented in various dilutions and a spectrophotometric or colorimetric response gives rapid quantitation.

In another embodiment of the invention, the nucleic acid sequences which encode MVBP may also be used to generate hybridization probes which are useful for mapping the naturally occurring genomic sequence. The sequences may be mapped to a particular chromosome or to a specific region of the chromosome using well known techniques . Such techniques include FISH, FACS, or artificial chromosome constructions, such as yeast artificial chromosomes, bacterial artificial chromosomes, bacterial P1 constructions or single chromosome cDNA libraries as reviewed in Price, C. M. (1993) Blood Rev. 7:127–134, and Trask, B. J. (1991) Trends Genet. 7:149–154.

FISH (as described in Verma et al. (1988) *Human Chromosomes: A Manual of Basic Techniques*, Pergamon Press, New York, N.Y.) may be correlated with other physical chromosome mapping techniques and genetic map data. Examples of genetic map data can be found in the 1994 Genome Issue of Science (265:1981f). Correlation between the location of the gene encoding MVBP on a physical chromosomal map and a specific disease , or predisposition to a specific disease, may help delimit the region of DNA associated with that genetic disease. The nucleotide sequences of the subject invention may be used to detect differences in gene sequences between normal, carrier, or affected individuals.

In situ hybridization of chromosomal preparations and physical mapping techniques such as linkage analysis using established chromosomal markers may be used for extending genetic maps. Often the placement of a gene on the chromosome of another mammalian species, such as mouse, may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region, for example, AT to 11q22–23 (Gatti, R. A. et al. (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier, or affected individuals.

In another embodiment of the invention, MVBP, its catalytic or immunogenic fragments or oligopeptides thereof, can be used for screening libraries of compounds in any of a variety of drug screening techniques. The fragment employed in such screening may be free in solution, affixed to a solid support, borne on a cell surface, or located intracellularly.

The formation of binding complexes, between MVBP and the agent being tested, may be measured.

Another technique for drug screening which may be used provides for high throughput screening of compounds having suitable binding affinity to the protein of interest as described in published PCT application WO84/03564. In this method, as applied to MVBP large numbers of different small test compounds are synthesized on a solid substrate, such as plastic pins or some other surface. The test compounds are reacted with MVBP, or fragments thereof, and washed. Bound MVBP is then detected by methods well known in the art. Purified MVBP can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding MVBP specifically compete with a test compound for binding MVBP. In this manner, the antibodies can be used to detect the presence of any peptide which shares one or more antigenic determinants with MVBP.

In additional embodiments, the nucleotide sequences which encode MVBP may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I cDNA Library Construction

The FIBRNGT01 cDNA library was constructed using 6 micrograms of polyA RNA isolated from a normal fibroblast cell line (GD23A). The cultured line was treated with 50 cGy of X-ray radiation, and RNA was collected 5 minutes after exposure. cDNA synthesis was initiated using an XhoI-oligo d(T) primer. Synthetic adapter oligonucleotides were ligated onto the cDNA enabling their insertion into the Stratagene Uni-ZAP™ vector system. Blue/white color selection allowed the detection of clones with cDNA insertions.

The fibroblast cDNA library was screened with either DNA or antibody probes and the pBluescript® phagemid (Stratagene) was rapidly excised in vivo. The phage particles were infected into *E. coli* host strain XL1-Blue® (Stratagene). Alternative unidirectional vectors include, but are not limited to, pcDNAI (Invitrogen, San Diego, Calif.) and pSHlox-1 (Novagen, Madison, Wis.).

II Isolation and Sequencing of cDNA Clones

The phagemid forms of individual cDNA clones were obtained by the in vivo excision process, in which the host bacterial strain was coinfected with both the λ library phage and an f1 helper phage. Polypeptides or enzymes derived from both the library-containing phage and the helper phage nicked the X DNA, initiated new DNA synthesis from defined sequences on the λ target DNA and created a smaller, single stranded circular phagemid DNA molecule that included all DNA sequences of the pBLUESCRIPT® plasmid and the cDNA insert. The phagemid DNA was secreted from the cells and purified, then used to re-infect fresh host cells, where double stranded phagemid DNA was produced. Because the phagemid carries the gene for β-lactamase, the newly transformed bacteria were selected on medium containing ampicillin.

Phagemid DNA was purified using the MAGIC MINI-PREPS™ DNA Purification System (Cat.#A7100, Promega, Madison, Wis.). This small-scale process provides a simple and reliable method for lysing the bacterial cells and rapidly isolating purified phagemid DNA using a proprietary DNA-binding resin. The DNA was eluted from the purification resin already prepared for DNA sequencing and other analytical manipulations.

Phagemid DNA was also purified using the QIAWELL-8 Plasmid, QIAWELL PLUS and QIAWELL ULTRA DNA Purification System (QIAGEN Inc. Chatsworth, Calif.). This product line provides a convenient, rapid and reliable high-throughput method for lysing the bacterial cells and isolating highly purified phagemid DNA in a multiwell format. The DNA was eluted from the purification resin and prepared for DNA sequencing and other analytical manipulations.

The cDNA inserts from random isolates of the cell library were sequenced in part using the methods of Sanger F and A Coulson (1975; J Mol Biol 94–441-). Methods for DNA sequencing are well known in the art. Conventional enzymatic methods employ DNA polymerase Klenow fragment, SEQUENASE™ or Taq polymerase to extend DNA chains from an oligonucleotide primer annealed to the DNA template of interest. Methods have been developed for the use of both single- and double-stranded templates. The chain termination reaction products are usually electrophoresed on urea-polyacrylamide gels and are detected either by autoradiography (for radionuclide-labelled precursors) or by fluorescence (for fluorescent-labeled precursors). Recent improvements in mechanized reaction preparation, sequencing and analysis using fluorescent detection methods include the Applied Biosystems 373 DNA sequencer and Catalyst 800.

The cDNA clones obtained from the library originate from essentially random initiation and termination events. Therefore, the reading frame contained within the clone might be, in some cases, ambiguous. In these cases, the reading frame can be ascertained by several types of analyses. First, reading frames contained within the coding sequence can be analyzed for the presence of start (ATG, GTG, etc.) and stop codons (TGA, TAA, TAG). Typically, one frame will continue throughout the major portion of all of a cDNA sequence and the other two pending frames tend to contain numerous stop codons. In these cases reading frame determination is straightforward. In other more difficult cases, frame determination may require further analysis. Algorithms for this purpose have been developed which analyze the occurrence of individual nucleotide bases at each putative codon triplet (e.g., Fickett, J. W. Nucleic Acids Research, 10, 5303 (1982)). Coding DNA tends to contain predominantly certain nucleotides within certain triplet periodicities, such as a significant preference for pyrimidines in the third codon position. These algorithms have been incorporated into widely available software and can be easily used to determine coding potential (and frame) of a given stretch of DNA. This algorithm-derived information, combined with start/stop codon information, can be used to determine proper frame with a high degree of certainty, thus permitting the correct reading frame alignment with appropriate expression vehicles.

IV Homology Searching of cDNA Clones and Deduced Proteins

Using the nucleotide sequences derived from the cDNA clones as query sequences (the sequences of the Sequence Listing), databases containing previously identified sequences are searched for areas of homology (similarity). Such databases include GenBank and EMBL. Two homology search algorithms were used. Homology algorithms help identify identical as well as only related sequences.

The first algorithm was originally developed by Lipman, D. J. and Pearson, W. R. (1985) Rapid and Sensitive Protein Similarity Searches, Science, 227:1435. In this algorithm, the homologous regions are searched in a two-step manner. In the first step, the highest homologous regions are determined by calculating a matching score using a homology score table. The parameter 'Ktup' is used in this step to establish the minimum window size to be shifted for comparing two sequences. Ktup also sets the number of bases that must match to extract the highest homologous region among the sequences. In this step, no insertions or deletions are applied and the homology is displayed as an initial (INIT) value.

In the second step, the homologous regions are aligned to obtain the highest matching core by inserting a gap in order to add a probable deleted portion. The matching score obtained in the first step is recalculated using the homology score Table and the insertion score Table to an optimized (OPT) value in the final output.

DNA homologies between two sequences can be examined graphically using the Harr method of constructing dot matrix homology plots (Needleman, S. B. and Wunsch, C. O. (1970) J. Mol. Biol 48:443). This method produces a two-dimensional plot which can be useful in determining regions of homology versus regions of repetition.

The second algorithm was developed by Applied Biosystems Inc. and has been incorporated into the Inherit 670 Sequence Analysis System. In this algorithm, Pattern Specification Language (developed by TRW Inc.) is used to determine regions of homology. There are three parameters that determine how the sequence comparisons are run: window size, window offset, and error tolerance. Using a combination of these three parameters, the DNA database is searched for sequences containing regions of homology and the appropriate sequences are scored with an initial value. Subsequently, these homologous regions are examined using dot matrix homology plots to determine regions of homology versus regions of repetition. Smith-Waterman alignments were used to display the results of the homology search.

Following the search for homologous nucleotide regions, the sequences from the cDNA clones were classified as to whether they are "exact" matches (most of the sequence is identical), homologous human matches (regions of high similarity, but not exact matches), homologous non-human matches (regions of significant similarity present in species other than human), or nonmatches (no significant regions of homology to previously identified nucleotide sequences).

Searches of the deduced polypeptides and peptides are done in a manner analogous to that done with the cDNA sequences. The sequence of the polypeptide is used as a query sequence and compared to the previously identified sequences contained in a database such as Swiss/Prot or the NBRF Protein database to find homologous polypeptides. These polypeptides are initially scored for homology using a homology score Table (Orcutt, B. C. and Dayhoff, M. O. (1985) Scoring Matrices, PIN Report MAT—0285 resulting in an INIT score. The homologous regions are aligned to obtain the highest matching scores by inserting a gap which adds a probable deleted portion. The matching score is recalculated using the homology score Table and the insertion score Table resulting in an optimized (OPT) score. In the absence of knowledge of the proper reading frame of an isolated sequence, the above-described polypeptide homology search may be performed by searching all 3 reading frames.

Peptide and polypeptide sequence homologies can also be ascertained using the INHERIT 670 Sequence Analysis System in an analogous way to that used in DNA sequence homologies. Pattern Specification Language and parameter windows are used to search polypeptide databases for sequences containing regions of homology which are scored with an initial value. Subsequent examination with a dot-matrix homology plot determines regions of homology versus regions of repetition.

IV Northern Analysis

Northern analysis is a laboratory technique used to detect the presence of a transcript of a gene and involves the hybridization of a labeled nucleotide sequence to a membrane on which RNAs from a particular cell type or tissue have been bound (Sambrook et al., supra).

Analogous computer techniques using BLAST (Altschul, S. F. 1993 and 1990, supra) are used to search for identical or related molecules in nucleotide databases such as Gen-Bank or the LIFESEQ™ database (Incyte Pharmaceuticals). This analysis is much faster than multiple, membrane-based hybridizations. In addition, the sensitivity of the computer search can be modified to determine whether any particular match is categorized as exact or homologous.

The basis of the search is the product score which is defined as:

$$\frac{\% \text{ sequence identity} \times \% \text{ maximum BLAST score}}{100}$$

The product score takes into account both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

The results of northern analysis are reported as a list of libraries in which the transcript encoding MVBP occurs. Abundance and percent abundance are also reported. Abundance directly reflects the number of times a particular transcript is represented in a cDNA library, and percent abundance is abundance divided by the total number of sequences examined in the cDNA library.

V Extension of MVBP-Encoding Polynucleotides

Nucleic acid sequence of Incyte Clone 148415 was used to design oligonucleotide primers for extending a partial nucleotide sequence to full length. One primer was synthesized to initiate extension in the antisense direction, and the other was synthesized to extend sequence in the sense direction. Primers were used to facilitate the extension of the known sequence "outward" generating amplicons containing new, unknown nucleotide sequence for the region of interest. The initial primers were designed from the cDNA using OLIGO 4.06 (National Biosciences), or another appropriate program, to be about 22 to about nucleotides in length, to have a GC content of 50% or more, and to anneal to the target sequence at temperatures of about 68° to about 72° C. Any stretch of nucleotides which would result in hairpin structures and primer-primer dimerizations was avoided.

Selected human cDNA libraries (Gibco/BRL) were used to extend the sequence If more than one extension is necessary or desired, additional sets of primers are designed to further extend the known region.

High fidelity amplification was obtained by following the instructions for the XL-PCR kit (Perkin Elmer) and thoroughly mixing the enzyme and reaction mix. Beginning with 40 pmol of each primer and the recommended concentrations of all other components of the kit, PCR was performed using the Peltier Thermal Cycler (PTC200; M.J. Research, Watertown, Mass.) and the following parameters:

| | |
|---|---|
| Step 1 | 94° C. for 1 min (initial denaturation) |
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat step 4–6 for 15 additional cycles |
| Step 8 | 94° C. for 15 sec |
| Step 9 | 65° C. for 1 min |
| Step 10 | 68° C. for 7:15 min |
| Step 11 | Repeat step 8–10 for 12 cycles |
| Step 12 | 72° C. for 8 min |
| Step 13 | 4° C. (and holding) |

A 5–10 μl aliquot of the reaction mixture was analyzed by electrophoresis on a low concentration (about 0.6–0.8%) agarose mini-gel to determine which reactions were successful in extending the sequence. Bands thought to contain the largest products were excised from the gel, purified using QIAQuick™ (QIAGEN Inc., Chatsworth, Calif.), and trimmed of overhangs using Klenow enzyme to facilitate religation and cloning.

After ethanol precipitation, the products were redissolved in 13 μl of ligation buffer, 1 μl T4-DNA ligase (15 units) and 1 μl T4 polynucleotide kinase were added, and the mixture was incubated at room temperature for 2–3 hours or overnight at 16° C. Competent E. coli cells (in 40 μl of appropriate media) were transformed with 3 μl of ligation mixture and cultured in 80 μl of SOC medium (Sambrook et al., supra). After incubation for one hour at 37° C., the E. coli mixture was plated on Luria Bertani (LB)-agar (Sambrook et al., supra) containing 2× Carb. The following day, several colonies were randomly picked from each plate and cultured in 150 μl of liquid LB/2× Carb medium placed in an individual well of an appropriate, commercially-available, sterile 96-well microtiter plate. The following day, 5 μl of each overnight culture was transferred into a non-sterile 96-well plate and after dilution 1:10 with water, 5 μl of each sample was transferred into a PCR array.

For PCR amplification, 18 μl of concentrated PCR reaction mix (3.3×) containing 4 units of rTth DNA polymerase, a vector primer, and one or both of the gene specific primers used for the extension reaction were added to each well. Amplification was performed using the following conditions:

| | |
|---|---|
| Step 1 | 94° C. for 60 sec |
| Step 2 | 94° C. for 20 sec |
| Step 3 | 55° C. for 30 sec |
| Step 4 | 72° C. for 90 sec |
| Step 5 | Repeat steps 2–4 for an additional 29 cycles |
| Step 6 | 72° C. for 180 sec |
| Step 7 | 4° C. (and holding) |

Aliquots of the PCR reactions were run on agarose gels together with molecular weight markers. The sizes of the PCR products were compared to the original partial cDNAs, and appropriate clones were selected, ligated into plasmid, and sequenced.

In like manner, the nucleotide sequence of SEQ ID NO:2 is used to obtain 5' regulatory sequences using the procedure above, oligonucleotides designed for 5' extension, and an appropriate genomic library.

VI Labeling and Use of Hybridization Probes

Hybridization probes derived from SEQ ID NO:2 are employed to screen cDNAs, genomic DNAs, or mRNAs. Although the labeling of oligonucleotides, consisting of about base-pairs, is specifically described, essentially the same procedure is used with larger cDNA fragments. Oligonucleotides are designed using state-of-the-art software such as OLIGO 4.06 (National Biosciences), labeled by combining 50 pmol of each oligomer and 250 $\mu$Ci of [$\gamma$-$^{32}$P] adenosine triphosphate (Amersham) and T4 polynucleotide kinase (DuPont NEN®, Boston, Mass.). The labeled oligonucleotides are substantially purified with Sephadex G-25 superfine resin column (Pharmacia & Upjohn). A portion containing $10^7$ counts per minute of each of the sense and antisense oligonucleotides is used in a typical membrane based hybridization analysis of human genomic DNA digested with one of the following endonucleases (Ase I, Bgl II, Eco RI, Pst I, Xba 1, or Pvu II; DuPont NEN®).

The DNA from each digest is fractionated on a 0.7 percent agarose gel and transferred to nylon membranes (Nytran Plus, Schleicher & Schuell, Durham, N.H.). Hybridization is carried out for 16 hours at 40° C. To remove nonspecific signals, blots are sequentially washed at room temperature under increasingly stringent conditions up to 0.1× saline sodium citrate and 0.5% sodium dodecyl sulfate. After XOMAT AR™ film (Kodak, Rochester, N.Y.) is exposed to the blots in a Phosphoimager cassette (Molecular Dynamics, Sunnyvale, Calif.) for several hours, hybridization patterns are compared visually.

VII Complementary Sequences or Antisense Molecules

Nucleic acid sequences complementary to the MVBP-encoding sequence or antisense molecules, or any part thereof, are used to inhibit in vivo or in vitro expression of naturally occurring MVBP. Although use of antisense oligonucleotides, comprising about 20 base-pairs, is specifically described, essentially the same procedure is used with larger cDNA fragments. A complementary oligonucleotide designed using computer programs well known in the art is used to inhibit expression of naturally occurring MVBP. The complementary oligonucleotide is designed from the most unique 5' coding sequence (SEQ ID NO:2) and used either to inhibit transcription by preventing promoter binding to the upstream nontranslated sequence or translation of an MVBP-encoding transcript by preventing the ribosome from binding. Using an appropriate portion of the signal and 5' sequence of SEQ ID NO:2, an effective antisense oligonucleotide includes any 15–20 nucleotides spanning the region which translates into the signal or 5' coding sequence of the polypeptide as shown in FIGS. 1A–D.

VIII Expression of MVBP

Expression of MVBP is accomplished by subcloning the cDNAs into appropriate vectors and transforming the vectors into host cells. In this case, a cloning vector such as pSport1, is used to express MVBP in *E. coli*. Upstream of the cloning site, this vector contains a promoter for β-galactosidase, followed by sequence containing the amino-terminal Met, and the subsequent seven residues of β-galactosidase. Immediately following these eight residues is a bacteriophage promoter useful for transcription and a linker containing a number of unique restriction sites.

Induction of an isolated, transformed bacterial strain with IPTG using standard methods produces a fusion protein which consists of the first eight residues of β-galactosidase, about 5 to 15 residues of linker, and the full length protein. The signal residues direct the secretion of MVBP into the bacterial growth media which can be used directly in the following assay for activity.

IX Demonstration of MVBP Activity

MVBP activity is tested using a vector which contains the nucleotide sequence for MVBP or a liposome containing purified protein. The vector or protein is introduced using state of the art methods into a cell culture and activity of the protein is assessed under a phase microscope by comparing the mitotic index of the cell culture prior to introduction of the sequence or protein with that obtained after introduction. Evaluation is made 24–48 hours after introduction of the nucleotide sequence and approximately 24 hours after introduction of the protein. Change in the mitotic index indicates MVBP is active.

X Production of MVBP Specific Antibodies

MVBP that is substantially purified using PAGE electrophoresis (Sambrook, supra), or other purification techniques, is used to immunize rabbits and to produce antibodies using standard protocols. The amino acid sequence deduced from SEQ ID NO:2 is analyzed using DNASTAR software (DNASTAR Inc) to determine regions of high immunogenicity and a corresponding oligopeptide is synthesized and used to raise antibodies by means known to those of skill in the art. Selection of appropriate epitopes, such as those near the C-terminus or in hydrophilic regions, is described by Ausubel et al. (supra), and others.

Typically, the oligopeptides are 15 residues in length, synthesized using an Applied Biosystems Peptide Synthesizer Model 431 A using fmoc-chemistry, and coupled to keyhole limpet hemocyanin (KLH, Sigma, St. Louis, Mo.) by reaction with N-maleimidobenzoyl-N-hydroxysuccinimide ester (MBS; Ausubel et al., supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radioiodinated, goat anti-rabbit IgG.

XI Purification of Naturally Occurring MVBP Using Specific Antibodies

Naturally occurring or recombinant MVBP is substantially purified by immunoaffinity chromatography using antibodies specific for MVBP. An immunoaffinity column is constructed by covalently coupling MVBP antibody to an activated chromatographic resin, such as CnBr-activated Sepharose (Pharmacia & Upjohn). After the coupling, the resin is blocked and washed according to the manufacturer's instructions.

Media containing MVBP is passed over the immunoaffinity column, and the column is washed under conditions that allow the preferential absorbance of MVBP (e.g., high ionic strength buffers in the presence of detergent). The column is eluted under conditions that disrupt antibody/MVBP binding (eg, a buffer of pH 2–3 or a high concentration of a chaotrope, such as urea or thiocyanate ion), and MVBP is collected.

XII Identification of Molecules Which Interact with MVBP

MVBP or biologically active fragments thereof are labeled with $^{125}$I Bolton-Hunter reagent (Bolton et al. (1973) Biochem. J. 133: 529). Candidate molecules previously arrayed in the wells of a multi-well plate are incubated with the labeled MVBP, washed and any wells with labeled MVBP complex are assayed. Data obtained using different concentrations of MVBP are used to calculate values for the number, affinity, and association of MVBP with the candidate molecules.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

```

What is claimed is:

1. An isolated and purified polynucleotide encoding a polypeptide comprising the amino acid sequence of SEQ ID NO:1.

2. A composition comprising the polynucleotide of claim 1 and a pharmaceutically acceptable carrier.

3. An isolated and purified polynucleotide comprising SEQ ID NO:2.

4. An isolated and purified polynucleotide which is fully complementary to the polynucleotide of claim 2.

5. A composition comprising the isolated and purified polynucleotide of claim 4 and a pharmaceutically acceptable carrier.

6. An expression vector containing the polynucleotide of claim 1.

7. A host cell containing the expression vector of claim 6.

8. A method for producing a polypeptide comprising the amino acid sequence of SEQ ID NO:1, the method comprising the steps of:

a) culturing the host cell of claim 7 under conditions suitable for the expression of the polypeptide; and
   b) recovering the polypeptide from the host cell culture.

* * * * *